(12) United States Patent
Liesenfelt et al.

(10) Patent No.: US 8,989,342 B2
(45) Date of Patent: Mar. 24, 2015

(54) METHODS AND SYSTEMS FOR VOLUMETRIC RECONSTRUCTION USING RADIOGRAPHY

(75) Inventors: Michael Liesenfelt, Knoxville, TN (US); Dan Shedlock, Knoxville, TN (US); William Talion Edwards, Foristell, MO (US)

(73) Assignee: The Boeing Company, Chicago, IL (US)

( * ) Notice: Subject to any disclaimer, the term of this patent is extended or adjusted under 35 U.S.C. 154(b) by 83 days.

(21) Appl. No.: 13/450,040

(22) Filed: Apr. 18, 2012

(65) Prior Publication Data

US 2013/0279645 A1    Oct. 24, 2013

(51) Int. Cl.
*H05G 1/60*   (2006.01)
*G01N 23/203*   (2006.01)

(52) U.S. Cl.
CPC .................................. *G01N 23/203* (2013.01)
USPC .............................................. 378/12; 378/19

(58) Field of Classification Search
CPC .... G01N 23/201; G01N 23/203; G01N 23/20
USPC .................... 378/6, 4, 7, 19, 70, 12
See application file for complete search history.

(56) References Cited

U.S. PATENT DOCUMENTS

| | | | | |
|---|---|---|---|---|
| 4,472,822 | A * | 9/1984 | Swift .............................. | 378/10 |
| 4,809,312 | A | 2/1989 | Annis | |
| 4,825,454 | A * | 4/1989 | Annis et al. ...................... | 378/87 |
| 5,070,455 | A * | 12/1991 | Singer et al. ...................... | 378/6 |
| 6,163,589 | A * | 12/2000 | Vartanian .......................... | 378/7 |
| 6,256,367 | B1 * | 7/2001 | Vartanian .......................... | 378/7 |
| 6,618,466 | B1 * | 9/2003 | Ning ............................... | 378/62 |
| 6,775,349 | B2 * | 8/2004 | Schotland et al. .............. | 378/21 |
| 7,418,073 | B2 * | 8/2008 | Schlomka et al. ................ | 378/6 |
| 7,551,709 | B2 * | 6/2009 | Schlomka et al. ................ | 378/6 |
| 7,551,718 | B2 | 6/2009 | Rothschild | |
| 7,646,850 | B2 * | 1/2010 | MacDonald ..................... | 378/87 |
| 7,912,180 | B2 * | 3/2011 | Zou et al. ......................... | 378/87 |
| 2004/0109532 | A1 * | 6/2004 | Ford et al. ........................ | 378/57 |
| 2004/0218714 | A1 | 11/2004 | Faust | |
| 2007/0189444 | A1 * | 8/2007 | Van Steven-Daal et al. ..... | 378/6 |
| 2008/0253524 | A1 * | 10/2008 | Boyden et al. ................... | 378/87 |
| 2009/0128557 | A1 | 5/2009 | Finlayson et al. | |
| 2009/0161818 | A1 * | 6/2009 | Sakurai et al. ................... | 378/15 |
| 2010/0140485 | A1 * | 6/2010 | Mishra et al. .............. | 250/363.1 |
| 2011/0249798 | A1 | 10/2011 | Rothschild | |

FOREIGN PATENT DOCUMENTS

WO        2009129488 A1    10/2009

OTHER PUBLICATIONS

GB Combined Search and Examination Report of application No. GB1306045.4; Aug. 8, 2008; 12 pages.
Wang et al., Analytic Reconstruction of Compton Scattering Tomography, Journal of Applied Physics, Aug. 1, 1999, pp. 1693-1698, vol. 86, No. 3.
Rigaud et al., Modeling and Simulation Results on a New Compton Scattering Tomography, available at http://perso-etis.ensea.fr/rigaud/publi/C/publi_pdf/C1.pdf, last visited Apr. 18, 2012.

* cited by examiner

*Primary Examiner* — Irakli Kiknadze
(74) *Attorney, Agent, or Firm* — Armstrong Teasdale LLP (57) ABSTRACT

Methods and systems for use in generating a volumetric reconstruction of an object using scattered X-ray radiography. An X-ray beam is directed towards a point within a target object. Scattered X-rays are measured by detectors and measurement data is stored. The X-ray beam is directed towards different points. Measurement data associated with each point is analyzed using a ray tracing methodology to assign contrast values to each point. A volumetric image is generated therefrom.

19 Claims, 8 Drawing Sheets

METHODS AND SYSTEMS FOR VOLUMETRIC RECONSTRUCTION USING RADIOGRAPHY

BACKGROUND

This invention relates generally to radiography, and more particularly to methods and systems for volumetric reconstruction using scattered X-ray radiography.

Radiography is sometimes used to generate volumetric, or three-dimensional, images of structures and systems when disassembly of the structures and systems is not desirable. For example, volumetric images may be used to service and repair aircraft, to detect foreign objects, and/or for reverse engineering purposes. Some known radiography systems use backscatter imaging to generate two-dimensional images that are a projection of a three-dimensional volume on an image plane. Such two-dimensional images cannot be used to generate three-dimensional images because the two-dimensional images lack depth information.

Some known systems for extracting depth information from backscatter images require collimation of a detector to limit return of the scattered X-rays from a specified depth. Detector collimation requires that the scan speed be reduced to collect enough scattered X-rays to produce an image with a sufficient signal to noise ratio. Also, because known systems are configured to penetrate to a particular depth, several scans have to be taken to produce an image with a significant depth of field. For example, imaging methods that include computed tomography generally rely on using geometry-processing algorithms to create a volumetric reconstruction from a series of two-dimensional transmission X-ray images. Transmission radiography is used to create a series of two-dimensional images from various perspectives about a central axis of an object, and relies on the assumption that photons will either pass through the object with zero scatter or be completely absorbed by the object. Because known computed tomography systems rely on transmission radiography, such systems require access to both sides (i.e., a front and a back side) of the subject object and therefore may be limited in use in some products, such as aircraft.

Accordingly, there is a need for radiography systems that enable volumetric reconstruction of objects without requiring access to both sides of the object. More particularly, there is a need for radiography systems capable of generating volumetric reconstructions of objects when only one side of the object is accessible.

BRIEF DESCRIPTION

In one aspect, a system is provided for use in generating a volumetric reconstruction of an object. The system includes an X-ray source configured to generate an X-ray beam and at least one detector capable of measuring X-rays scattered from the X-ray beam, wherein each detector is positioned in a pre-determined orientation with respect to the X-ray source. The system also includes a computing device programmed to instruct the X-ray source to transmit the X-ray beam towards the object, receive, from each detector, measurement data representative of scattered X-rays measured by each detector, and generate a volumetric image of the object using a projection of the measurement data into the object.

In another aspect, a method is provided for use in generating a volumetric reconstruction of an object. The method includes transmitting an X-ray beam from an X-ray source towards the object, measuring X-rays scattered from the X-ray beam using at least one detector positioned in a pre-determined orientation with respect to the X-ray source, receiving, using a computing device, measurement data representative of the measured scattered X-rays from the at least one detector, and generating a volumetric image of the object using a projection of the measurement data into the object.

In yet another aspect, one or more non-transitory computer-readable media having computer-executable components embodied thereon are provided. The computer-executable components include a scanning control component that when executed by at least one processor unit causes the processor unit to instruct an X-ray source to transmit an X-ray beam towards an object, a data collection component that when executed by at least one processor unit causes the processor unit to receive measurement data representative of X-rays scattered from the X-ray beam measured by at least one detector, wherein the at least one detector is positioned in a pre-determined orientation with respect to the X-ray source, and a volumetric reconstruction component that when executed by at least one processor unit causes the processor unit to generate a volumetric image of the object using a projection of the measurement data into the object.

The features, functions, and advantages that have been discussed can be achieved independently in various embodiments or may be combined in yet other embodiments further details of which can be seen with reference to the following description and drawings.

DETAILED DESCRIPTION

Embodiments described herein facilitate the volumetric reconstruction of objects using scattered X-ray radiography. More particularly, embodiments described herein enable a three-dimensional ("3D") image or volumetric reconstruction of an object to be generated from scattered X-rays.

Three-dimensional data is acquired by directing an X-ray beam into an object. One or more detectors are configured to measure the scattered X-rays produced by the X-ray beam in the object. X-rays are directed into the object from a plurality of angles and/or positions such that the one or more detectors may measure the scattered X-rays from a plurality of perspectives. Data collected by the detectors and a pre-determined geometry of the detectors with respect to the X-ray source are used to generate a 3D image of the object.

The 3D image of the object may be generated using a 3D extension of the two-dimensional ("2D") Radon Back Projection. A ray tracing methodology is used to assign contrast values to a subset of 3D points. Each subset of 3D points is determined by defining the volume of points contained in a geometry defined by the intersection of a single detector's field of view and a cone representing the penetrating path of the X-ray beam through the object. The contrast of each point in the subset is defined by the corresponding pixel contrast value from the respective 2D image produced by each detector. The contrast of each point within the target object is determined by averaging the contrast value of that point from each subset.

Figure 1:
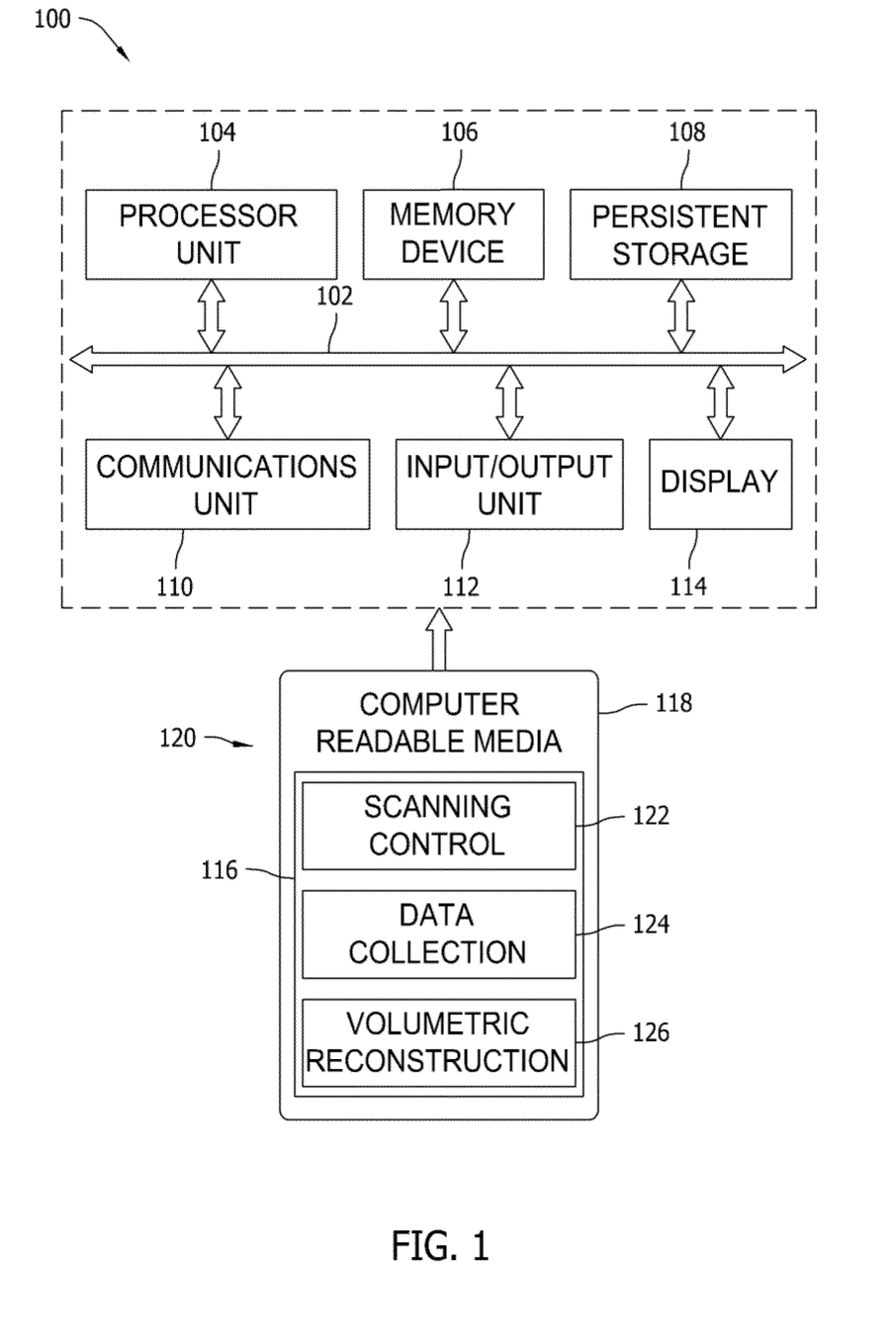
FIG. 1 is a block diagram of an exemplary computing device.

FIG. 1 is a block diagram of an exemplary computing device 100. In the exemplary embodiment, computing device 100 includes communications fabric 102 that enables communications between a processor unit 104, a memory 106, persistent storage 108, a communications unit 110, an input/output (I/O) unit 112, and a presentation interface, such as a display 114. In addition to, or in the alternative to, the presentation interface may include an audio device (not shown) and/or any device capable of conveying information to a user. Display 114 may include 3D displays and/or projectors capable of presenting 3D information to a viewer, e.g., using 3D glasses or other suitable 3D presentation systems.

Processor unit 104 executes instructions for software that may be loaded into memory 106. Processor unit 104 may be a set of one or more processors, or may include multiple processor cores, depending on the particular implementation. Further, processor unit 104 may be implemented using one or more heterogeneous processor systems in which a main processor is present with secondary processors on a single chip. In another embodiment, processor unit 104 may be a homogeneous processor system containing multiple processors of the same type.

Memory 106 and persistent storage 108 are examples of storage devices. As used herein, a storage device is any piece of hardware that is capable of storing information either on a temporary basis and/or a permanent basis. Memory 106 may be, for example, without limitation, a random access memory and/or any other suitable volatile or non-volatile storage device. Persistent storage 108 may take various forms depending on the particular implementation, and persistent storage 108 may contain one or more components or devices. For example, persistent storage 108 may be a hard drive, a flash memory, a rewritable optical disk, a rewritable magnetic tape, and/or some combination of the above. The media used by persistent storage 108 also may be removable. For example, without limitation, a removable hard drive may be used for persistent storage 108.

A storage device, such as memory 106 and/or persistent storage 108, may be configured to store data for use with the processes described herein. For example, a storage device may store computer-executable instructions, executable software components (e.g., scanning control, data collection, and/or volumetric reconstruction components), stored data from X-ray detectors, generated volumetric images, and/or any other information suitable for use with the methods described herein.

Communications unit 110, in these examples, provides for communications with other computing devices or systems. In the exemplary embodiment, communications unit 110 is a network interface card. Communications unit 110 may provide communications through the use of either or both physical and wireless communication links.

Input/output unit 112 enables input and output of data with other devices that may be connected to computing device 100. For example, without limitation, input/output unit 112 may provide a connection for user input through a user input device, such as a keyboard and/or a mouse. Further, input/output unit 112 may send output to a printer. Display 114 provides a mechanism to display information, such as any information described herein, to a user. For example, a presentation interface such as display 114 may display a graphical user interface, such as those described herein.

Instructions for the operating system and applications or programs are located on persistent storage 108. These instructions may be loaded into memory 106 for execution by processor unit 104. The processes of the different embodiments may be performed by processor unit 104 using computer implemented instructions and/or computer-executable instructions, which may be located in a memory, such as memory 106. These instructions are referred to herein as program code (e.g., object code and/or source code) that may be read and executed by a processor in processor unit 104. The program code in the different embodiments may be embodied on different physical or tangible computer-readable media, such as memory 106 or persistent storage 108.

Program code 116 is located in a functional form on non-transitory computer-readable media 118 that is selectively removable and may be loaded onto or transferred to computing device 100 for execution by processor unit 104. Program code 116 and computer-readable media 118 form computer program product 120 in these examples. In one example, computer-readable media 118 may be in a tangible form, such as, for example, an optical or magnetic disc that is inserted or placed into a drive or other device that is part of persistent storage 108 for transfer onto a storage device, such as a hard drive that is part of persistent storage 108. In a tangible form, computer-readable media 118 also may take the form of a persistent storage, such as a hard drive, a thumb drive, or a flash memory that is connected to computing device 100. The tangible form of computer-readable media 118 is also referred to as computer recordable storage media. In some instances, computer-readable media 118 may not be removable.

Alternatively, program code 116 may be transferred to computing device 100 from computer-readable media 118 through a communications link to communications unit 110 and/or through a connection to input/output unit 112. The communications link and/or the connection may be physical or wireless in the illustrative examples. The computer-readable media also may take the form of non-tangible media, such as communications links or wireless transmissions containing the program code.

In some illustrative embodiments, program code 116 may be downloaded over a network to persistent storage 108 from another computing device or computer system for use within computing device 100. For instance, program code stored in a computer-readable storage medium in a server computing device may be downloaded over a network from the server to computing device 100. The computing device providing program code 116 may be a server computer, a workstation, a client computer, or some other device capable of storing and transmitting program code 116.

Program code 116 may be organized into computer-executable components that are functionally related. For example, program code 116 may include one or more scanning control components 122, data collection components 124, volumetric reconstruction components 126, and/or any component suitable for practicing the methods described herein. Each component may include computer-executable instructions that, when executed by processor unit 104, cause processor unit 104 to perform one or more of the operations described herein. In exemplary embodiments, scanning control component 122 causes processor unit 104 to control one or more scanning operations by controllably directing an X-ray beam into a target object. Data collection component 124 causes processor unit 104 to collect data produced by scanning operations. Volumetric reconstruction component 126 causes processor unit 104 to analyze collected data for generating a volumetric reconstruction.

The different components illustrated herein for computing device 100 are not meant to provide architectural limitations to the manner in which different embodiments may be implemented. The different illustrative embodiments may be implemented in a computer system including components in addition to or in place of those illustrated for computing device 100. For example, other components shown in FIG. 1 can be varied from the illustrative examples shown.

In one example, a storage device in computing device 100 is any hardware apparatus that may store data. Memory 106, persistent storage 108 and computer-readable media 118 are examples of storage devices in a tangible form.

In another example, a bus system may be used to implement communications fabric 102 and may include one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, without limitation, memory 106 or a cache such as that found in an interface and memory controller hub that may be present in communications fabric 102.

Figure 2:
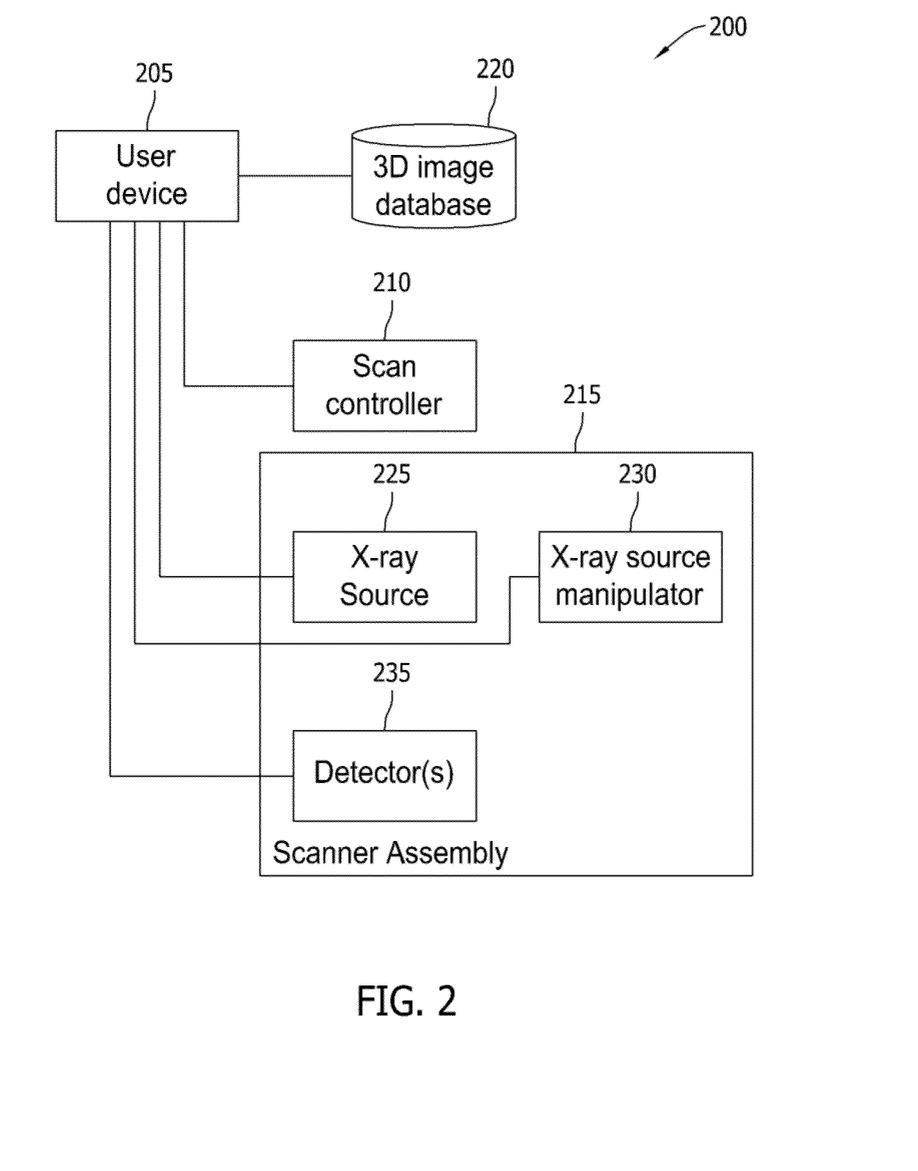
FIG. 2 is a block diagram illustrating an exemplary system that may be used in volumetric reconstruction of an object using scattered X-ray radiography.

FIG. 2 is a block diagram illustrating an exemplary system 200 that may be used in volumetric reconstruction of an object using scattered X-ray radiography. System 200 includes a user device 205, a scan controller 210, a scanner assembly 215, and a 3D image database 220. Scanner assembly 215 includes an X-ray source 225, an X-ray source manipulator 230, and at least one detector 235. In exemplary embodiments, user device 205 and 3D image database 220 are each a computing device 100. Alternatively, both user device 205 and 3D image database 220 may be a single computing device 100.

User device 205 is communicatively coupled to scan controller 210, X-ray source 225, X-ray source manipulator 230, and to detectors 235. Scan controller 210 is coupled to scanner assembly 215 and is capable of selectably positioning (i.e., translating, rotating, etc.) and/or orienting scanner assembly 215, as described in more detail herein. Alternatively, scanner assembly 215 may be positioned manually. X-ray source 225 is capable of controllably, e.g., by user device 205, emitting a beam of X-ray radiant energy. X-ray source manipulator 230 controllably, e.g., by user device 205, orients X-ray source 225 for selectably directing the X-ray beam emitted from X-ray source 225. In other words, X-ray source 225 may be selectably positioned, e.g., using X-ray source manipulator 230, with respect to detectors 235 while detectors 235 remain stationary, or detectors 235 may be positioned with X-ray source 225, e.g., using scan controller 210. User device 205 is programmed to measure and/or calculate the orientation and/or distance of x-ray source 225 with respect to each detector 235, referred to herein as a "pre-determined orientation."

X-ray source manipulator 230 and/or X-ray source 225 may include a collimator (not shown). Detectors 235 are capable of detecting X-rays and photons thereof and producing electrical signals representative of detected X-rays. For example, detectors 235 may include a scintillator and/or a semiconductor array detector, such as an indirect flat panel detector. User device 205 is programmed to scan the object using scanner assembly 215, store the data in 3D image database 220, analyze the data in 3D image database 220, and generate a 3D image.

Figure 3:
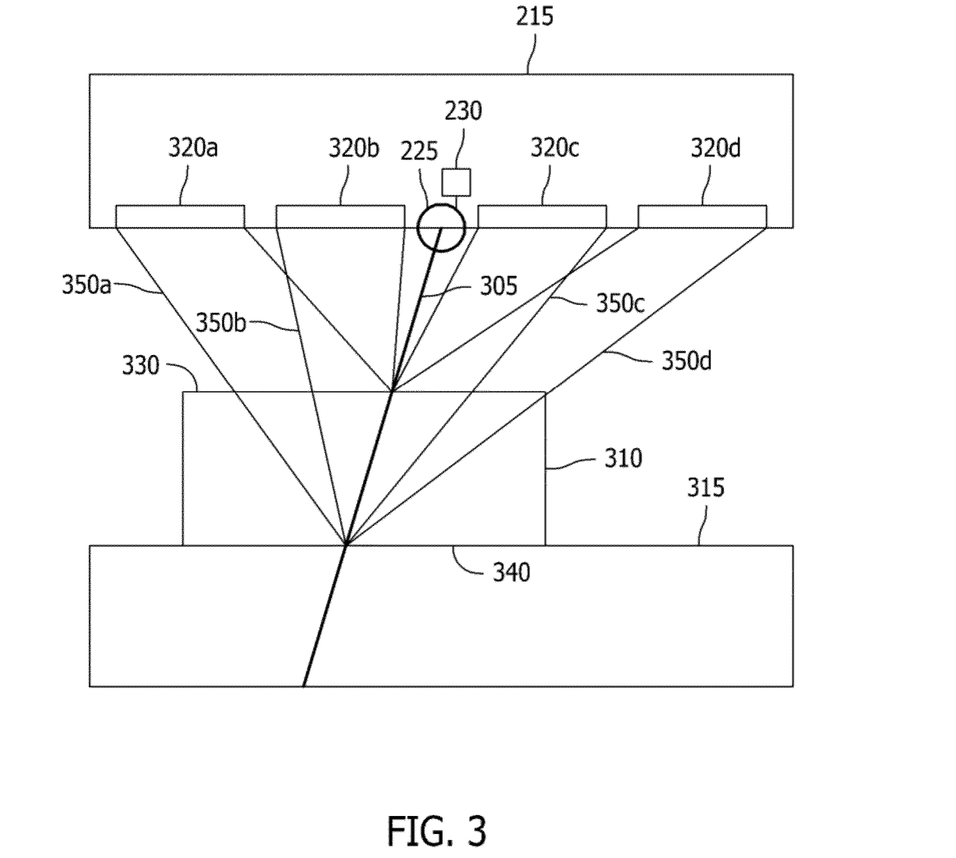
FIG. 3 illustrates an exemplary configuration of the system in FIG. 2.

FIG. 3 illustrates an exemplary configuration of system 200 (shown in FIG. 2). In the exemplary embodiment, a beam 305 of X-ray radiant energy is emitted from X-ray source 225 towards a pre-determined scan target volume 310 that includes a target object (not shown). The target object may be, but is not necessarily, positioned on a support surface 315, such as aluminum. Beam 305 is a narrow cone beam or a pencil beam. In the exemplary embodiment, scanner assembly 215 includes a first detector 320*a*, a second detector 320*b*, a third detector 320*c*, and a fourth detector 320*d*, e.g., detectors 235, and is positioned proximate to target volume 310. Detectors 320 each have a pre-determined distance and orientation with respect to X-ray source 225. Although four detectors are shown in FIG. 3, it should be appreciated that any number of detectors may be used in accordance with the methods and systems described herein. Detectors 320 may be arranged in a grid, e.g., a 2×2 grid, in a line, or in any configuration that enables system 200 to function as described herein.

Beam 305 substantially penetrates target volume 310, including the target object, causing X-rays, or photons, (not shown) to be scattered. At least some scattered X-rays travel towards, and are detected by, detectors 320. More particularly, at least a portion of beam 305 enters target volume 310 through a first side 330, and at least a portion of beam 305 penetrates target volume 310 to a second side 340. Detectors 320 are positioned such that scattered photons exiting the target object through first side 330 can be detected by detectors 320, i.e. backscattered X-rays. Alternatively, or additionally, one or more detectors 320 may be positioned to detect scattered X-rays exiting the target object through any number of sides.

Figure 4:
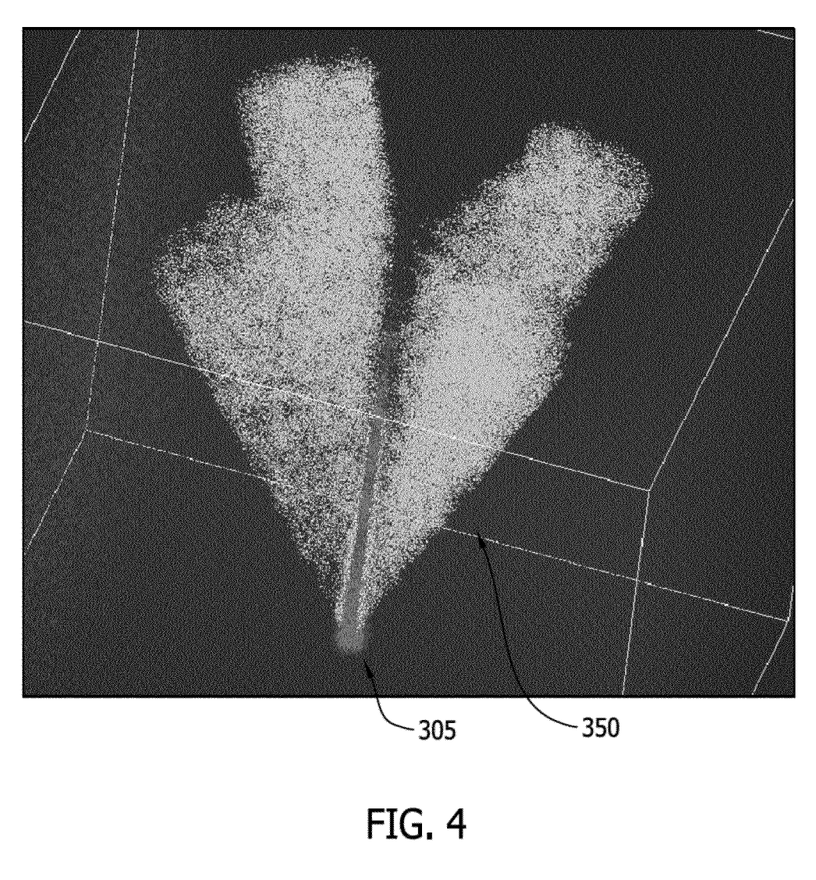
FIG. 4 illustrates an exemplary X-ray beam and scattered X-rays that may be produced using the system in FIG. 2.

Scattered X-rays travel from beam 305 to respective detectors 320 through a volume 350*a-d* to each respective detector 320. FIG. 4 illustrates beam 305 entering a target object. Volumes 350 of scattered photons are illustrated as originating at beam 305 and terminating at detectors (not shown in FIG. 4).

Figure 5:
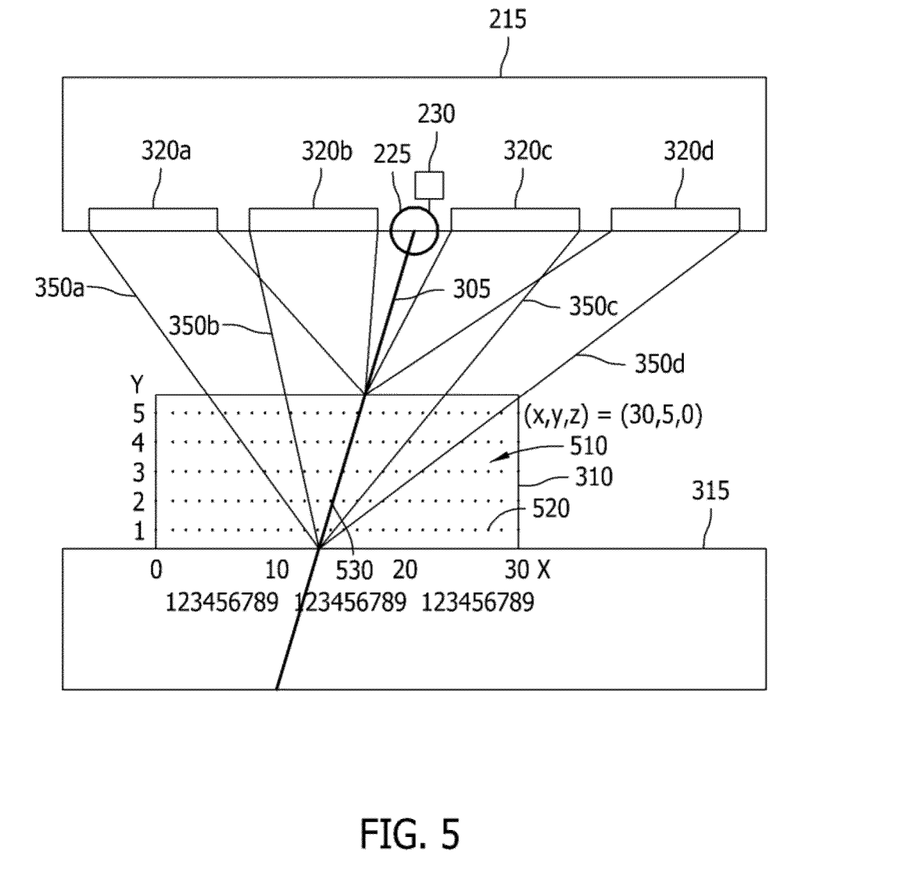
FIG. 5 illustrates an exemplary configuration of the system in FIG. 2 including a point cloud.

FIG. 5 illustrates system 200 of FIG. 2 including a point cloud 510 for analyzing target volume 310. Point cloud 510 is a collection of points 520 in the three-dimensional space defined by target volume 310. As explained in more detail herein, system 200 generates 3D information about the target object by collecting data associated with each point 520 in point cloud 510. Point cloud 510 may include points 520 both inside and outside of the target object, and portions of the target object may not be included in point cloud 510. In the exemplary embodiment, points 520 in point cloud 510 are regularly-spaced. Alternatively, or additionally, point cloud 510 may include randomly generated points, e.g., using a monte carlo method. Point cloud 510 may include any number of points, e.g., millions of points, that enables system 200 to function as described herein.

Point cloud 510 enables discrete collection and storage of data associated with target volume 310. For example, point cloud 510 may be represented as a data structure, e.g., using user device 205, and/or stored in a database, e.g., 3D image database 220. The position of each point 520 in point cloud 510 is stored. Data collected for each point 520 is stored and associated with the corresponding point 520 in point cloud 510. More particularly, the position, an accumulated contrast value, and/or a total photon count may be stored for each point 510 in point cloud 520. Data collected by detectors 320 for a particular point 520 may be stored separately (i.e., for each detector 320) or cumulatively. Alternatively to a point cloud, information about target volume 310 may be stored in a voxel set.

During operation, X-ray beam 305 from X-ray source 235 is directed towards a first point 530 in point cloud 510. Photons are scattered by the target object towards detectors 320 through volumes 350. Detectors 320 collect data about first point 530 including a photon count from photons in volumes 350 and/or photon energy information for each photon. Detectors 320 transmit data about first point 350 to user device 205 (shown in FIG. 2) for collection, storage, and/or analysis. In like manner, X-rays are directed at each point 520 in point cloud 510 and data is collected for each point 520.

Figure 6:
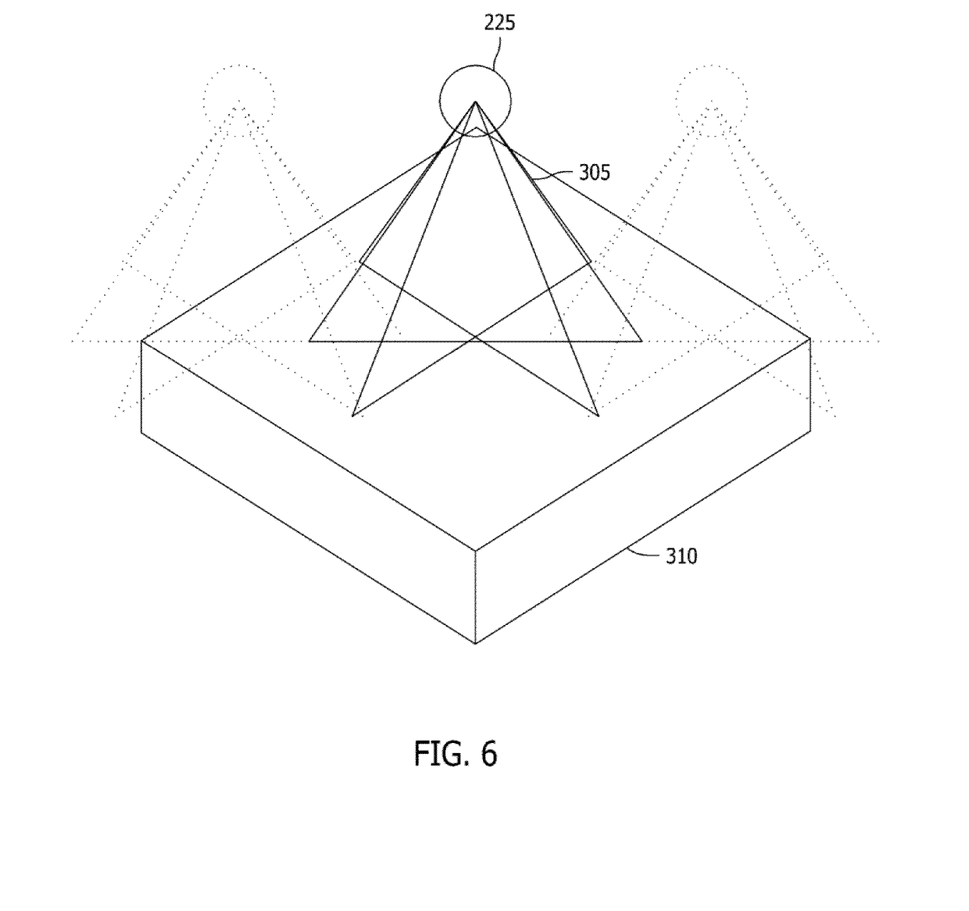
FIG. 6 illustrates an exemplary translation of an X-ray source used with the system in FIG. 2.
Figure 7:
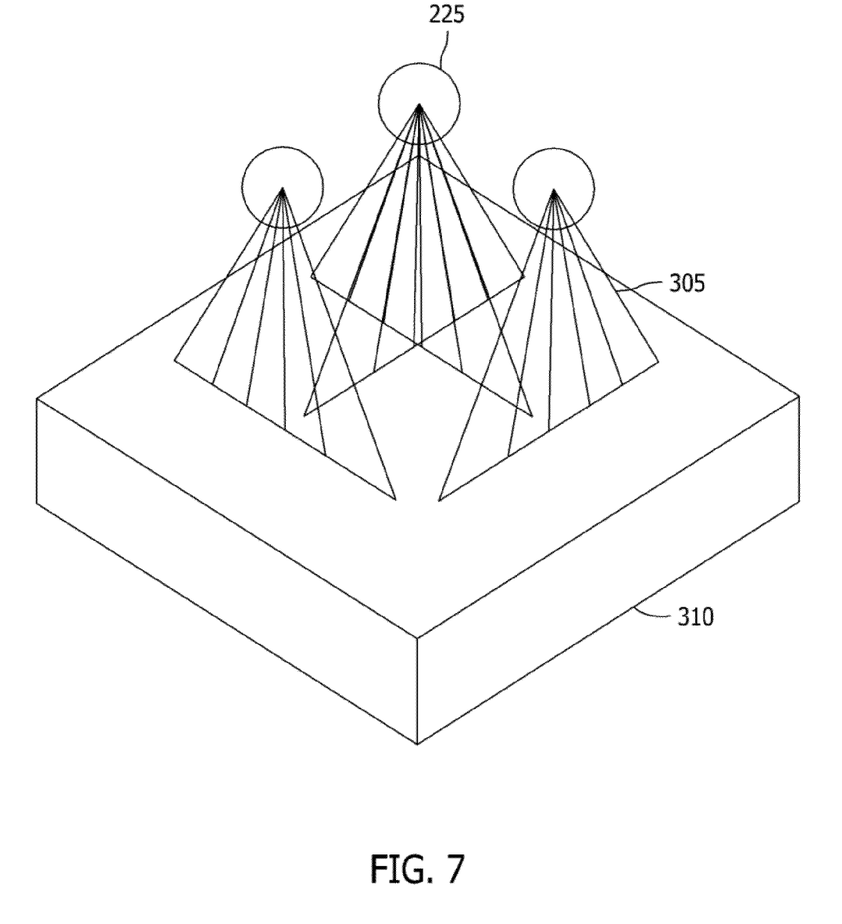
FIG. 7 illustrates an exemplary rotation of an X-ray source used with the system in FIG. 2.

X-ray beam 305 may be directed towards points 520 in point cloud 510 by orienting X-ray source 225, e.g., using X-ray source manipulator 230, such that beam 305 is swept through target volume 310. X-ray source 225 may be directed by controllably orienting, e.g., using X-ray source manipulator 230, the X-ray source collimator (not shown). Alternatively, or additionally, X-ray source 225, together with scanner assembly 215, may be translated, e.g., using scan controller 210, to new positions with respect to target volume 310, as illustrated in FIG. 6, and/or rotated such that a plane in which beam 305 is swept is rotated, as illustrated in FIG. 7. Conducting scans (i.e., X-ray emissions from X-ray source 225 and data collections using detectors 320) from more than one perspective facilitates generating 3D images by collecting data with an increased orthogonality factor with respect to target volume 310.

Data collected from target volume 310 is analyzed to generate a 3D image of the target object in target volume 310. When X-ray beam 305 travels through an object, all single scattered photons hitting each detector 320 originate from a ray trace of the beam within the object. As beam 305 is directed towards each point 520 in point cloud 510, the angle of beam 305 with respect to target volume 310 changes. Volumes 350 produced by adjacent and neighboring points 520, as beam 305 iterates through point cloud 310, may partially overlap. The 3D image is generated by analyzing the overlapped space generated from a plurality of points 520 and angles.

More particularly, the 3D image is generated using a ray tracing methodology to back-project data collected by detectors 320 into the target object. Contrast values are assigned to a subset of points 520 assumed to be contained in a particular volume 350. Each subset of points is determined by defining the volume of points contained in a geometry defined by the intersection of a single detector's field of view and a cone representing the transmission path of X-ray beam 305 through an object. The contrast of each point 520 in this subset is defined by the corresponding pixel contrast value from the respective 2D image produced by each detector 320. The individual valued subsets are combined into a single point set by averaging the contrast value at each point 520 in point cloud 510. Average contrast values may be determined by weighting the data from each detector 320 to account for differences in detector size, type, position, material. The assigned contrast value represents a scattering-to-absorption ratio, and is used to generate the 3D image.

Figure 8:
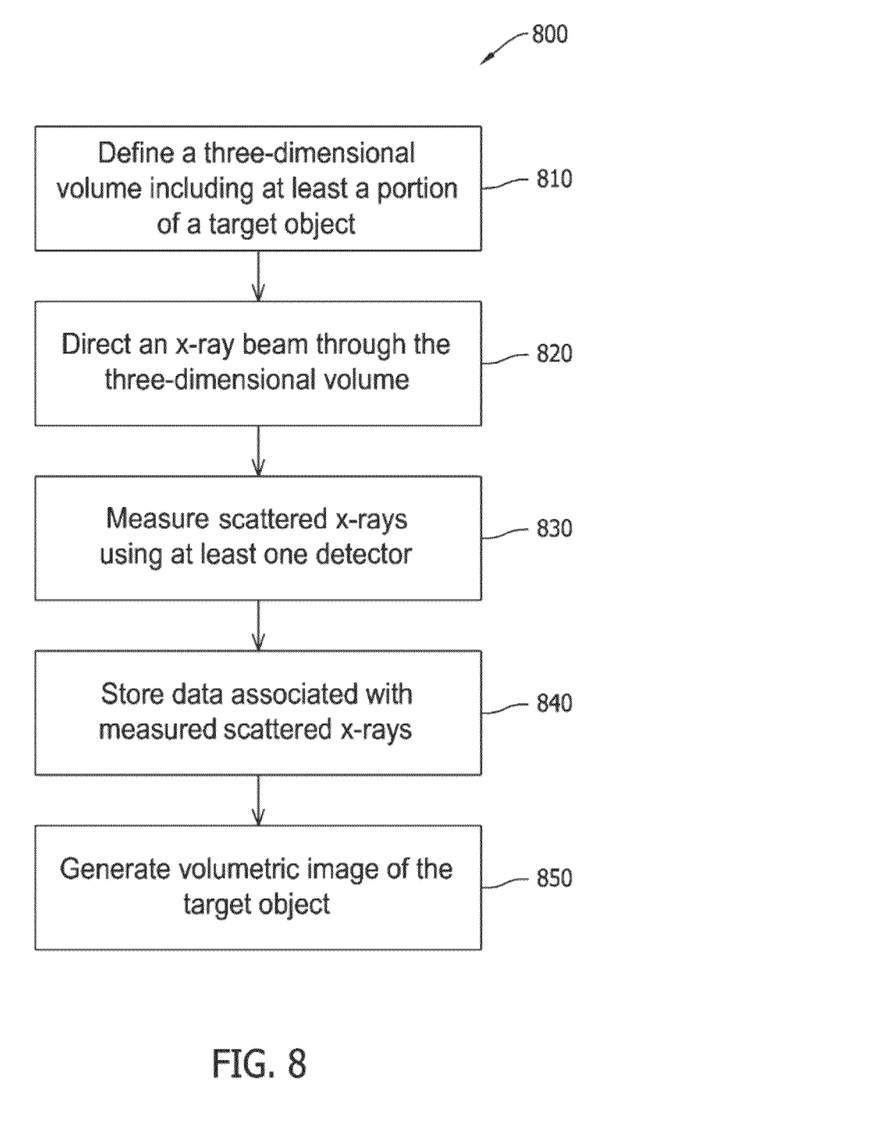
FIG. 8 is a flowchart of an exemplary method that may be used to generate a volumetric reconstruction of an object using the system in FIG. 2.

FIG. 8 illustrates an exemplary method 800 for use with system 200 (shown in FIG. 2). A 3D volume, e.g., target volume 310, is defined 810 that includes at least a portion of a target object. A point distribution, e.g., point cloud 510, may be created throughout the 3D volume. The point distribution may be regularly-spaced or randomly distributed.

An X-ray beam is directed 820 through the 3D volume. The beam is moved and/or swept through the 3D volume in order to create scattered X-rays from a variety of perspectives. Scattered X-rays are measured 830 using at least one detector. The at least one detector generates a photon count. Data associated with the measured scattered X-rays is stored 840. The data is analyzed and a volumetric image of the target object within the three-dimensional volume is generated 850. More particularly, the detector response of each detector is back projected into the 3D volume. Each back projection may be analyzed as a separate perspective. Contrast values may be assigned to each point in the point distribution based on the back projection. Contrast values are combined to generate the 3D image. The 3D image may be output, e.g., by communications unit 110, input/output unit 112, and/or display 114.

Accordingly, exemplary embodiments enable the volumetric reconstruction of a target object using scattered X-ray radiography. As compared to known apparatus and systems that are used for volumetric reconstruction, the above-described systems and methods enable volumetric reconstruction using detectors positioned on the same side of a target object as an X-ray source, and are operable in less time. More specifically, an X-ray beam is directed through a pre-determined 3D volume that includes a target object. Scattered X-rays from the target object are measured by detectors. Data from each detector is stored and analyzed. By back projecting each detector response, volumetric information can be determined for the target object.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for use in generating a volumetric reconstruction of an object, said system comprising:

an X-ray source configured to generate an X-ray beam, said X-ray source positioned on a first side of the object;

at least one detector capable of measuring X-rays scattered from the X-ray beam, said at least one detector positioned on the first side of the object in a pre-determined orientation with respect to said X-ray source; and a computing device programmed to:

define a point cloud including a plurality of points associated with a three-dimensional (3D) space, wherein at least a portion of the object is within the 3D space;

instruct said X-ray source to sweep the X-ray beam across the plurality of points;

receive, from said at least one detector, measurement data for each point of the plurality of points, the measurement data representative of scattered X-rays associated with the X-ray beam and measured by said at least one detector;

assign a contrast value to each point in a subset of the plurality of points, the subset determined by defining a volume of points included within a geometry defined by an intersection of a field of view of the at least one detector and a penetrating path of the X-ray beam through the object; and generate a volumetric image of the object using a projection of the measurement data for the plurality of points into the object.

2. A system in accordance with claim 1, wherein said X-ray source comprises a collimator.

3. A system in accordance with claim 1, wherein said detector comprises a scintillator and a semiconductor array detector.

4. A system in accordance with claim 1, wherein said computing device is communicatively coupled to a database, said computing device is further programmed to store measurement data in said database.

5. A system in accordance with claim 1, wherein said computing device is further programmed to output the generated volumetric image.

6. A system in accordance with claim 1, wherein the contrast value assigned to each point in the subset of the plurality of points is associated with a corresponding pixel contrast value from a respective image produced by the at least one detector.

7. A system in accordance with claim 1, wherein said computing device is further programmed to combine the points assigned a contrast value into a single point set by averaging the contrast value of each point defined in the point cloud.

8. A method for use in generating a volumetric reconstruction of an object, said method comprising:
    defining a point cloud including a plurality of points associated with a three-dimensional (3D) space, wherein at least a portion of the object is within the 3D space;
    sweeping an X-ray beam from an X-ray source across the plurality of points, the X-ray source positioned on a first side of the object;
    measuring X-rays scattered from the X-ray beam using at least one detector positioned on the first side of the object in a pre-determined orientation with respect to the X-ray source;
    receiving, using a computing device, measurement data for each point of the plurality of points, the measurement data representative of the measured scattered X-rays associated with the X-ray beam and measured by the at least one detector;
    assigning a contrast value to each point in a subset of the plurality of points, the subset determined by defining a volume of points included within a geometry defined by an intersection of a field of view of the at least one detector and a penetrating path of the X-ray beam through the object; and
    generating a volumetric image of the object using a projection of the measurement data for the plurality of points into the object.

9. A method in accordance with claim 8, further comprising controllably positioning the X-ray source using a scan controller coupled to the X-ray source.

10. A method in accordance with claim 9, wherein controllably positioning the X-ray source using a scan controller comprises instructing, using the computing device, the scan controller to position the X-ray source.

11. A method in accordance with claim 10, wherein controllably positioning the X-ray source using a scan controller further comprises at least one of rotating and translating the X-ray source.

12. A method in accordance with claim 8, wherein transmitting an X-ray beam from an X-ray source towards the object comprises transmitting an X-ray beam from an X-ray source towards the object using a collimator.

13. A method in accordance with claim 8, wherein measuring scattered X-rays from the X-ray beam using at least one detector comprises measuring scattered X-rays from the X-ray beam using at least one detector including a scintillator and a semiconductor array detector.

14. A method in accordance with claim 8, further comprising storing, using the computing device, the measurement data in a database communicatively coupled to the computing device.

15. A method in accordance with claim 8, further comprising outputting, using the computing device, the generated volumetric image.

16. One or more non-transitory computer-readable media having computer-executable components embodied thereon, said computer-executable components comprising:
    a point definition component that when executed by at least one processor unit causes the processor unit to define a point cloud including a plurality of points associated with a three-dimensional (3D) space, wherein at least a portion of the object is within the 3D space;
    a scanning control component that when executed by at least one processor unit causes the processor unit to instruct an X-ray source to sweep an X-ray beam across the plurality of points, the X-ray source positioned on a first side of the object;
    a data collection component that when executed by at least one processor unit causes the processor unit to receive measurement data for each point of the plurality of points, the measurement data representative of X-rays scattered from the X-ray beam measured by at least one detector, wherein the at least one detector is positioned on the first side of the object in a pre-determined orientation with respect to the X-ray source; and
    a volumetric reconstruction component that when executed by at least one processor unit causes the processor unit to:
    assign a contrast value to each point in a subset of the plurality of points, the subset determined by defining a volume of points included within a geometry defined by an intersection of a field of view of the at least one detector and a penetrating path of the X-ray beam through the object; and
    generate a volumetric image of the object using a projection of the measurement data for the plurality of points into the object.

17. One or more non-transitory computer-readable media in accordance with claim 16, wherein said data collection component causes the processor unit to store the measurement data in a database, and wherein said scanning control component causes the processor unit to instruct a scan controller coupled to the X-ray source to controllably position the X-ray source.

18. One or more non-transitory computer-readable media in accordance with claim 16, wherein said volumetric reconstruction component causes the processor unit to generate a back projection of the measurement data based on a pre-determined orientation of the at least one detector with respect to the X-ray source.

19. One or more non-transitory computer-readable media in accordance with claim 16, wherein said volumetric reconstruction component causes the processor unit to output the volumetric image.

* * * * *